United States Patent [19]
Rhodes et al.

[11] Patent Number: 5,495,763
[45] Date of Patent: Mar. 5, 1996

[54] METHOD FOR RESONANT MEASUREMENT

[76] Inventors: George W. Rhodes, 5201 Rio Grande Blvd., N.W., Albuquerque, N.M. 87107; Albert Migliori, Rte. 4, Box 258 Tano Rd., Sante Fe, N.M. 87501; Raymond D. Dixon, 396 Connie Ave., White Rock, N.M. 87544

[21] Appl. No.: 75,159

[22] Filed: Jun. 10, 1993

[51] Int. Cl.$^6$ .................................................. G01H 13/00
[52] U.S. Cl. ............................................. 73/579; 73/602
[58] Field of Search ........................... 73/579, 602, 593, 73/645, 646, 659

[56] References Cited

U.S. PATENT DOCUMENTS 5,355,731  10/1994  Dixon ........................................ 73/579

OTHER PUBLICATIONS

Visscher, et al., "Vibration of elastic objects", J. Acoust. Soc. Am., vol. 90, No. 4, Pt. 1, Oct. 1991, pp. 2156–2162.

*Primary Examiner*—Thomas P. Noland
*Assistant Examiner*—Christine K. Oda

[57] ABSTRACT

A method of measurement of objects to determine object flaws, Poisson's ratio ($\sigma$) and shear modulus ($\mu$) is shown and described. First, the frequency for expected degenerate responses is determined for one or more input frequencies and then splitting of degenerate resonant modes are observed to identify the presence of flaws in the object. Poisson's ratio and the shear modulus can be determined by identification of resonances dependent only on the shear modulus, and then using that shear modulus to find Poisson's ratio using other modes dependent on both the shear modulus and Poisson's ratio.

5 Claims, 1 Drawing Sheet

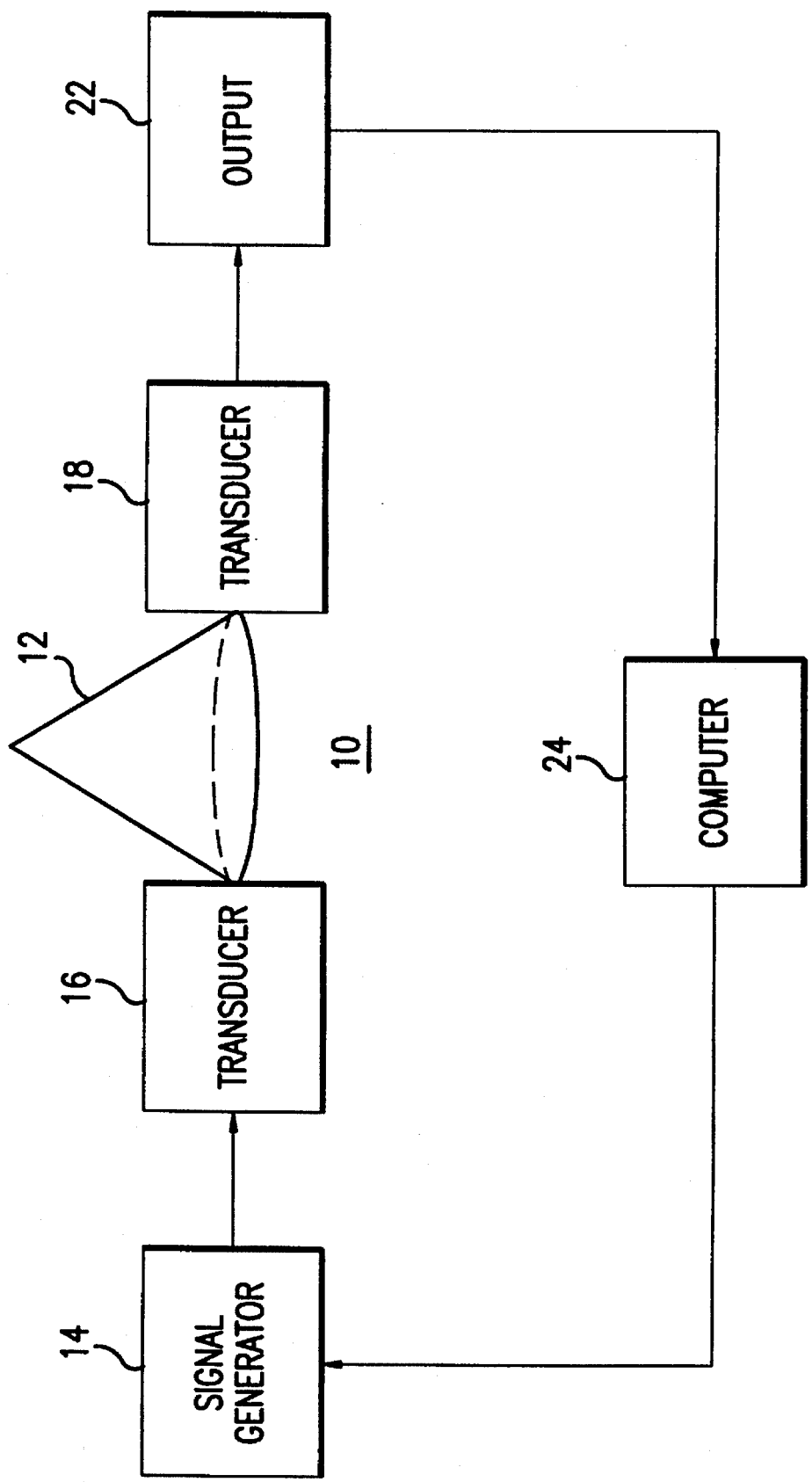

METHOD FOR RESONANT MEASUREMENT

This invention was made with government support under Contract No. W-7405-ENG-36 awarded by the U.S. Department of Energy. The government has certain rights in the invention.

BACKGROUND OF INVENTION

1. Field of the Invention

This invention relates to nondestructive testing and, more particularly, to nondestructive detection of flaws in objects. A flaw may be a crack in an object, a void in an object, and/or a deviation from dimensional specifications of the object, and any other parameter that causes a change in mechanical resonance.

2. The Prior Art

Computational procedures have been developed to find the mechanical resonances of objects other than a sphere but which also have some symmetries. This work is described in "On the modes of free vibrations on inhomogeneous and anisotropic elastic objects" by Visscher et al., J. Acoust Soc. Am., 90 (4) p. 2154, 1991. Examples are, objects, such as a cylinder, rectangular parallel piped, cone, ellipsoid, or pyramids with regular polygon bases.

SUMMARY OF THE INVENTION

This invention relates to a method of determination of flaws in an object. The flaws may be in the form of surface or subsurface cracks, tolerance errors, voids inside of the object or any other physical characteristics which would separate otherwise degenerate resonant frequencies. In the method of this invention, the existence and frequencies of degenerate resonant vibrational modes are first calculated or predicted by means of a mathematical analysis of the object to be tested. The object is then examined by exciting it with a mechanical transducer such that the excitation frequency is slowly varied from one predetermined frequency to another. From the prediction, modes are identified that should be degenerate (i.e. several modes will vibrate at precisely the same frequency) in an unflawed object. If flaws exist, the degenerate modes are resolved (or split) into two or more closely spaced resonances. Objects exhibiting resolved or split modes are identified as flawed or defective.

In this invention, applicant also provides for measurement of the shear modulus ($\mu$) and Poisson's ratio ($\sigma$), both of which are dependant upon frequencies.

Testing of objects by use of sound (including ultrasound) and vibrations is well known. The prior art is extensive and encompasses many types of non-destructive testing. Resonant sound and ultrasound has also been used for testing purposes as described in U.S. Pat. Nos. 5,062,296 and 4,976,148.

To achieve the foregoing and other objects, and in accordance with the purposes of the present invention, as embodied and broadly described herein, the process of this invention is a method for testing objects based on their vibrational response. To achieve this, a vibrational (sound) spectrum is mathematically generated for an object, and is also measured. Comparison of the two enables detection of defective objects.

The detection of the flaws described above is addressed by the present invention and a resonant ultrasound spectroscopy (RUS) technique is presented for examining all of the objects made in a production run. It is therefore an object of the present invention to provide for inspecting objects at rates consistent with a manufacturing process.

A further object of the present invention is to provide an object inspection process that characterizes the entire body regardless of orientation in an inspection device.

It is another object of the present invention to provide an inspection technique that provides high sensitivity to certain flaws.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate an embodiment of the present invention and, together with the description, serve to explain the principles of the invention.

FIG. 1 shows a block diagram of a testing apparatus in accordance of this invention.

DETAILED DESCRIPTION OF THE INVENTION

In accordance with the present invention resonant ultrasound spectroscopy (RUS) provides a rapid and accurate method for determining object deviations from specifications. A new technique for using RUS is provided. Quick inspection of objects determines their acceptability from a quality acceptance standpoint. Inspection is possible for certain objects too difficult to inspect by any other means at rates consistent with operation of a typical production line. Thus, product quality is assured, not estimated, and production manufacturing trends can be identified and corrected before quantities of defective products are manufactured.

In application Ser. No. 880,393, filed May 8, 1992 now U.S. Pat. No. 5,355,731, entitled, "Sphericity Determination Using Resonant Ultrasound Spectroscopy" (incorporated herein by reference), there is described a method of analysis which is specific to sphericity determination. One mode of employment of RUS relates the resonant ultrasound spectrum of a component to the dimensions and material properties of the components. As used herein, RUS can be used for determining some dimensions of certain symmetric objects.

FIG. 1 depicts a simplified schematic of a system 10 for generating and analyzing the RUS spectrum of a conical object 12. The object geometry may be any one which can be mathematically described. Signal generator 14 excites transducer 16 for vibrating cone 12 over a predetermined frequency range, e.g., between 4 and 4000 kHz. The response of cone 12 is detected by transducer 18 and supplied to an output amplifier 22. A suitable RUS system 10 is described in U.S. Pat. No. 4,976,148, issued Dec. 11, 1990, to Migliori, et al. (incorporated here in by reference). The outputs from amplifier 22 are input to computer 24 for analysis and computation of the difference between the cone 12 resonant vibrational modes and those of a perfect cone.

In an overview of the present method, RUS spectra for the vibrational modes of a perfect object are computed as a function of shear modulus and Poisson's ratio. A RUS spectrum is obtained from a production object and components of the spectrum, i.e., the degenerate resonant modes, are identified from the perfect object calculations. The shear modulus and Poisson's ratio for the production object can then be determined by comparing the identified and calculated degenerate resonances of a homogeneous isotropic elastic object.

When an object deviates from perfect, at least some of the degenerate resonant frequencies become split, i.e., the resonant frequencies split into multiple resonant frequencies. The resonance deviations arising from splitting in the resonant frequencies is generally linear near the degenerate resonant frequencies as a function of the distortion.

Other nonuniformities in the manufactured object such as cracks or internal voids will also affect the RUS spectrum such that a defective object can be detected. Further, drifts in manufacturing parameters can be detected and corrected before large lots of deviant material are produced.

In a patent application Ser. No. 880,393 (Filed May 8, 1992), now U.S. Pat. No. 5,355,731, it was demonstrated that spherical objects exhibit degenerate resonant modes. If the spherical symmetry is broken by a flaw, crack, or subsurface defect, the degeneracy is such that what appeared to be a single resonance becomes split into several distinct resonances. This splitting is used quantitatively to determine errors in sphericity, while the resonances themselves are used to determine density, diameter or elastic moduli depending on which two of these three quantities are known.

By examining resonances in regions predicted to exhibit degeneracies, splittings into two or more peaks are observed when a flaw is introduced. In addition, computational procedures, such as finite-element analysis can be applied to objects that are not simple geometric shapes but which still have cylindrical, conical, or other symmetries. These objects exhibit only a few degeneracies but they are adequate to find flaws. Accidental degeneracies in objects have also been observed in objects that are not in general expected to have any degeneracies but which exhibit them only because certain small changes in dimensions can bring otherwise disparate resonances into conjunction. Thus the current method can also be applied to many objects that are not expected to have degenerate modes, but nonetheless exhibit one or more degenerate resonances. The mode density (number of resonances per unit frequency interval) is, for any object, approximately proportional to the cube of the frequency. Thus as resonance measurements are made at higher and higher frequencies, the density of resonances rapidly increases. Eventually, the width of each individual resonance is greater than the spacing between resonances so that they run together. This is called the reverberation limit. Below this limit, but well above the frequency of the first resonance lies a region where there are many well separated resonances. If the ultrasonic attenuation of the material is low, as it is in most metals, ceramics, glasses and other materials, then the intermediate region will consist of hundreds of well-separated resonances. It is usually the case that some of these hundreds of resonances are separated by 0.1% or less in frequency. By judicious changes in the dimension or shape of the object some of the closely spaced modes can be made to coincide. Because only very small changes are required, almost any manufactured object can be forced to have accidental degeneracies that do not affect the function of the object. Any object that exhibits degeneracies can be tested using resonances.

Finite-element mathematical models that are readily available for complex, asymmetric objects can, under many circumstances, predict the mode type of the degenerate mode and predict its shift with internal or surface flaws, moduli or density (and thus temperature as well) to obtain quantitative information about the flaw size or tolerance error.

In addition to the detection of flaws, we can use a surprising and heretofore unknown property of mechanical resonances to determine the elastic moduli of the material used in the object. This property is that all elastically isotropic objects exhibit many resonances that depend only on the shear modulus. Thus, if the shear modulus ($\mu$) and Poisson's ratio ($\sigma$) are desired for an elastically isotropic object for which measurements and computations have been made, a very simple procedure can be used to find both $\mu$ and $\sigma$. This is of value because often the material properties are important for the correct functioning of the object under test. Below the region where there are hundreds of resonances, there exists a region just above the first resonance where only a few well-separated modes are present. Using any of the above mentioned computations, we can determine which of these modes depends only on $\mu$. For any mode at frequency $f_m$ that is dependent only on $\mu$ we scale the shear modulus as follows:

$$\mu' = \mu(f_m/f_c)^2$$

where ($\mu'$) is the actual (new) shear modulus, $\mu$ is the one used in the computation, $f_m$ is the measured frequency, $f_c$ is the computed frequency. Next, the resonances using the new value for $\mu'$ can be computed. At this point the shear modulus is determined, and all the modes dependent only on $\mu'$ will agree with the measurement, to an accuracy approximately equal to dimensional tolerances of the object. The modes that do not agree are the modes that depend on both shear modulus ($\mu$) and Poisson's ratio ($\sigma$). We now use the new $\mu'$ to compute $df_c/d\sigma$ using any of a number of the usual numerical procedures to compute derivatives for another mode at frequency $f_{m1}$ that is not in agreement with the measurement. We can now determine ($\sigma'$), the actual (new) Poisson's ratio as follows:

$$\sigma' = \sigma(df_c/d\sigma)(f_{m1} - f_{c1}) \qquad \text{Equation (1)}$$

where $f_{c1}$ is the computed mode that corresponds to $f_{m1}$ the measured mode dependent on calculated Poisson's ratio ($\sigma$).

Because for any resonance at frequency f for an elastically isotropic object, $$df = \delta d_i(\partial f/\partial d_i) - \tfrac{1}{2}(\delta\rho) + \tfrac{1}{2}(\delta\mu) + df/d\sigma)\delta\sigma \qquad \text{Equation (2)}$$

where $\rho$ is the density, $d_i$ are all the dimensions necessary to describe the object and the implied summation over repeated indices convention is used. It is clear that one cannot determine density ($\rho$) and shear modulus ($\mu$) independently because f depends in exactly opposite ways on these quantities.

However, if a particular material such as a ceramic has a reasonably well known relationship between shear modulus ($\mu$) and density ($\rho$), then one can combine the terms in equation (2) that contain $\mu$ and $\rho$. A measurement of at least as many resonances as there are unknowns in equation (2) will yield the dimensional, density and modulus errors without the need for any other independent measurements of any one of these quantities. If only one dimension is needed to describe the object (such as the edge of a cube, or the diameter of a sphere), or if a tolerance error is present that has exactly the same percentage error for all the dimensions of the object is present, than an additional measurement must be used. Thus, a set of resonances can be used to provide tolerance errors, flaw detection and material properties simultaneously in many elastically isotropic objects.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determination of flaws in objects comprising the steps of:
   a. mathematically determining degenerate modes having degenerate resonant frequencies of a mathematical model of said object;
   b. examining object resonances in at least one region predicted to exhibit degeneracy;
   c. observing a splitting of degenerate modes of said object resonances into at least two peaks;
   d. identifying objects which exhibit splitting of degenerate modes into at least two peaks as flawed, and
   e. computing and measuring degenerate modes which are dependent only on the shear modulus in step a.

2. A method for determination of flaws in objects comprising the steps of:
   a. mathematically determining degenerate modes having degenerate resonant frequencies of a mathematical model of said object;
   b. examining object resonances in at least one region predicted to exhibit degeneracy;
   c. observing a splitting of degenerate modes of said object resonances into at least two peaks;
   d. identifying objects which exhibit splitting of degenerate modes into at least two peaks as flawed, and
   e. computing and measuring degenerate modes which are dependent on both the shear modulus and Poisson's ratio in step a.

3. A method for determination of flaws in objects comprising the steps of:
   a. mathematically determining degenerate modes having degenerate resonant frequencies of a mathematical model of said object;
   b. examining object resonances in at least one region predicted to exhibit degeneracy;
   c. observing a splitting of degenerate modes of said object resonances into at least two peaks;
   d. identifying objects which exhibit splitting of degenerate modes into at least two peaks as flawed; and
   e. determining the actual shear modulus ($\mu'$) by the following relationship after step b:

$$\mu' = \mu \left[ \frac{f_m}{f_c} \right]^2$$

where $\mu$ equals computed shear modulus, $f_m$= measured frequency from step b, and $f_c$=computed frequency from step a.

4. The method in accordance with claim 3, further comprising the step of computing the actual (new) Poisson's ratio ($\sigma'$) in accordance with the following formula:

$$\sigma' = \sigma \left[ \frac{df_c}{d\sigma} \right] (f_{m1} - f_{c1})$$

wherein $f_{c1}$ is a computed mode that corresponds to $f_{m1}$, a measured mode dependent upon calculated Poisson's ratio ($\sigma$).

5. A method for determining the existence of flaws in an object comprising the steps of:
   a. calculating at least one frequency region at which there is a degenerate resonant mode frequency of said object;
   b. applying vibrations to said object at frequencies within said at least one frequency region;
   c. identifying the presence of splitting of a degenerate resonant mode frequency into at least two degenerate resonant modes,
   d. determining that a flaw exists in said object when presence of splitting of calculated degenerate resonant mode is identified; and
   e. repeating the steps of applying, identifying and determining at a plurality of different calculated frequencies.

* * * * *